United States Patent
Overstreet et al.

(10) Patent No.: US 11,033,717 B2
(45) Date of Patent: Jun. 15, 2021

(54) CATHETER ANCHOR SYSTEM AND METHOD THEREOF

(71) Applicant: TENSION SQUARE, LLC, Sarasota, FL (US)

(72) Inventors: Mychael Arnell Overstreet, Sarasota, FL (US); Sonya Yvonne Overstreet, Harker Heights, TX (US)

(73) Assignee: TENSION SQUARE, LLC, Sarasota, FL (US)

(*) Notice: Subject to any disclaimer, the term of this patent is extended or adjusted under 35 U.S.C. 154(b) by 145 days.

(21) Appl. No.: 16/027,300

(22) Filed: Jul. 4, 2018

(65) Prior Publication Data
US 2019/0046771 A1 Feb. 14, 2019

Related U.S. Application Data

(60) Provisional application No. 62/543,428, filed on Aug. 10, 2017.

(51) Int. Cl.
*A61M 25/02* (2006.01)
*A61F 13/00* (2006.01)
(Continued)

(52) U.S. Cl.
CPC ........... *A61M 25/02* (2013.01); *A61B 5/0215* (2013.01); *A61B 5/035* (2013.01); *A61B 5/6832* (2013.01);
(Continued)

(58) Field of Classification Search
CPC .......... A61M 25/02; A61M 2025/0273; A61M 2025/024–026; A61M 2005/1586;
(Continued)

(56) References Cited

U.S. PATENT DOCUMENTS 4,838,878 A 6/1989 Kalt et al.
5,163,914 A 11/1992 Abel
(Continued)

OTHER PUBLICATIONS

Talreja et al., Endoluminal dilatation for embedded hemodialysis catheters: A case-control study of factors associated with embedding and clinical outcomes, PLoS One. Mar. 27, 2017, vol. 12, No. 3, pp. 1-8.

(Continued)

*Primary Examiner* — Bhisma Mehta
*Assistant Examiner* — John J Crawford
(74) *Attorney, Agent, or Firm* — The Roy Gross Law Firm, LLC; Roy Gross

(57) ABSTRACT

A method and system of and for securing a lumen or catheter, after placement in a patient, to prevent unwanted removal or dislodgement of the lumen or catheter caused by patient movement and/or further medical interventions such as cardiopulmonary chest compressions, electrical defibrillation, surgical procedures, and the like. The method and system comprising simple and sterile materials that preclude the use of excessive suturing and ineffective ad-hoc methods with tape and gauze. The catheter is secured by a rubber on plastic frictional force and will resist external forces while preventing the tube structure from bending and subsequent occlusion. The device can be comfortably attached to the patient in all of the anatomical locations typically targeted for large catheter installment. The method of securement is rapid and requires only a single personnel to handle the device and the catheter tube simultaneously.

17 Claims, 12 Drawing Sheets

(51) Int. Cl.
    *A61M 25/00*     (2006.01)
    *A61B 5/0215*     (2006.01)
    *A61M 5/158*     (2006.01)
    *A61B 5/03*     (2006.01)
    *A61J 15/00*     (2006.01)
    *A61B 5/00*     (2006.01)

(52) U.S. Cl.
    CPC ......... *A61B 5/6833* (2013.01); *A61J 15/0061* (2013.01); *A61M 5/158* (2013.01); *A61M 25/0017* (2013.01); *A61F 2013/00412* (2013.01); *A61J 15/0015* (2013.01); *A61M 2005/1586* (2013.01); *A61M 2025/0246* (2013.01); *A61M 2025/0273* (2013.01); *A61M 2210/101* (2013.01); *A61M 2210/1017* (2013.01)

(58) Field of Classification Search
    CPC .... A61M 2210/101; A61M 2210/1017; A61M 25/0017; A61M 2025/0366; A61M 2025/0253; A61M 2025/0293; A61B 5/0215; A61B 5/6831–6832; A61F 2013/00412; A61J 15/0061; A61J 15/0034; A61J 15/0053
    See application file for complete search history.

(56) References Cited

U.S. PATENT DOCUMENTS

| | | | |
|---|---|---|---|
| 5,215,532 A * | 6/1993 | Atkinson | A61M 25/02 128/DIG. 26 |
| 5,292,312 A * | 3/1994 | Delk | A61M 25/02 128/DIG. 26 |
| 5,354,283 A * | 10/1994 | Bark | A61M 25/02 128/DIG. 26 |
| 5,395,344 A * | 3/1995 | Beisang, III | A61M 25/02 128/DIG. 26 |
| 5,800,402 A | 9/1998 | Bierman | |
| 6,132,399 A | 10/2000 | Shultz | |
| 6,213,979 B1 * | 4/2001 | Bierman | A61M 25/02 128/DIG. 26 |
| 6,387,076 B1 | 5/2002 | Landuyt | |
| 6,569,121 B1 | 5/2003 | Purow et al. | |
| 7,749,199 B2 | 7/2010 | Mogg | |
| 8,251,957 B2 | 8/2012 | Kyvik et al. | |
| 9,248,259 B2 | 2/2016 | Kyvik et al. | |
| 9,486,613 B2 | 11/2016 | Dickert et al. | |
| 10,086,168 B2 * | 10/2018 | Olson | A61M 27/00 |
| 2007/0249980 A1 * | 10/2007 | Carrez | A61M 25/02 602/47 |
| 2008/0200880 A1 | 8/2008 | Kyvik et al. | |
| 2010/0106114 A1 * | 4/2010 | Weston | A61M 1/0088 604/319 |
| 2012/0245529 A1 | 9/2012 | Hummen et al. | |
| 2012/0330255 A1 | 12/2012 | Carlin | |
| 2014/0207072 A1 | 7/2014 | Nokes, Jr. et al. | |
| 2015/0119808 A1 | 4/2015 | Khalaj | |
| 2015/0367102 A1 | 12/2015 | Andino et al. | |
| 2016/0114103 A1 * | 4/2016 | Burke | A61M 5/1415 604/179 |
| 2016/0114135 A1 | 4/2016 | Jaouani | |
| 2020/0038631 A1 * | 2/2020 | O'Sullivan | A61M 25/02 |

OTHER PUBLICATIONS

Burying The Peritoneal Dialysis Catheter, Mitch Medical Healthcare » Laparoscopic Urology, accessed on Dec. 4, 2018, Retrieved from <https://www.mitchmedical.us/laparoscopic-urology/burying-the-peritoneal-dialysis-catheter.html>.

Maritz et al., A novel way to secure a chest drain, Ann R Coll Surg Engl. Jan. 2014, vol. 96, No. 1, p. 82.

* cited by examiner

CATHETER ANCHOR SYSTEM AND METHOD THEREOF

CROSS-REFERENCE TO RELATED APPLICATION

This application claims the benefit of U.S. Provisional Application No. 62/543,428, filed Aug. 10, 2017, the contents of which is incorporated herein by reference in its entirety.

FIELD OF THE INVENTION

The present invention is directed to a method and system of and for securing a lumen or catheter, after placement in a patient, to prevent unwanted removal or dislodgement of the lumen or catheter caused by patient movement and/or further medical interventions such as cardiopulmonary resuscitation and the like. The securing of lumen and catheters in current practice is accomplished by suturing or in some cases supplemented with basic materials on hand like tape and gauze, rather than dedicated devices; therefore, this is a growing field with few well-established methods.

BACKGROUND OF THE INVENTION

Medical lumens or catheters are generally used to infuse a patient trans-natural-orifice or intravenously with medicative fluids, and/or for removing from a patient, urine, blood, or other fluids. A longtime and common problem after placing a catheter is securing or anchoring the catheter at or near its entry/exit point to prevent unwanted and possibly life threating removal or dislodgment of the lumen or catheter. A very common technique used to attempt to mitigate such unwanted removal is to use so-called "medical tape" in almost unlimited configurations in an attempt to "tape the catheter" to the patient. Such is typically effective with narrow diameter lumens catheters such as used for intravenous infusion at a patient's hand or forearm.

However, many specialized catheters or lumens are placed subcutaneously, such as but not limited to feeding tubes (i.e. jejunum or gastrostomy catheters or tubes and intrapleural catheters used to remove fluids or air from the thoracic cavity)(TABLE 1). It is difficult to tape these types of catheters or lumens to patients. Additionally, it is detrimental to the catheter or lumen's function if a "kink" or bend is inadvertently introduced during taping.

So-called "chest tubes" are typically placed via a thoracotomy; an incision between and/or through the ribs into the thoracic cavity. Once a catheter, lumen, or tube is inserted through a thoracotomy; typically, the tube is secured to the patient's skin with a surgical clamp, sutures, or adhesive patches or tape. However, these are limited methods of adhesion especially if further medical interventions are applied such as surgical procedures, cardiopulmonary chest compressions, electrical defibrillation, and the like.

A further variable related to medical catheters and lumens is the degree of arc or curve of the catheter as it enters/exits a patient. Related to intrapleural catheters or tubes, such are typically large in diameter and may be easily occluded or kinked if immediately bent and secured to a patient's chest. For a lack of an effective and efficient anchoring or securing means; many medical professionals utilize rolls of medical gauze around or beside the catheter and then secure with medical tape. However, such "ad hoc" methods are extremely ineffective for their intended purpose and use.

Known methods and systems used to various degrees of success in securing or anchoring an inserted catheter include: U.S. Pat. Nos. 4,838,878, 5,163,914, 5,292,312, 5,800,402, 6,132,399, 6,132,399, 6,387,076, 6,569,121, 7,749,199, 8,251,957, 9,248,259, 9,486,613, US20080200880, US20120245529, US20140207072, US20150119808, US20150367102, US20160114135.

It has been taught in medical practice that tape and gauze are the best means available at the moment. However, the "tape and gauze" method inevitably fails every time. The tape and gauze method does not attach firmly to the patient's chest for any length of time. The tape and gauze are bulky to the point of aiding in dislodgment and getting in the way of other definitive treatments such as CPR, defibrillation and EKG placement. Moreover, the tape and gauze method creates a bulky mass that is easily snagged or grabbed inadvertently in the heat of the moment. Lastly, the tape and gauze method requires more than one person and takes up precious moments of transport time.

It is desired to provide a catheter anchor method and system that efficiently secures medical devices to a patient. It is further desired to provide a method and system to overcome the above-mentioned and other disadvantages in the prior art.

SUMMARY OF THE INVENTION

It is an object of the present invention to provide a method and system of and for providing an anchor method and system for a medical device, such as a catheter.

It is an object of the present invention to provide a method and system of and for providing an anchor that is readily attached to patients and rapidly secured to different types of catheters or lumen.

It is an object of the present invention to provide a method and system of and for securing a catheter or lumen to a patient without bending or occluding flow through the catheter or lumen.

It is an object of the present invention to provide a method and system to secure a catheter to patient after a chest decompression has been performed.

It is an object of the present invention to provide a method and system to save time in securing a catheter to a patient while allowing full utilization of the catheter or lumen without interference with other treatments.

It is an object of the present invention to provide a method and system to secure a medical device, such as a Turkel system, at various lengths to a patient.

Objects of the invention are achieved by providing an apparatus for securing a medical device to a patient during a medical procedure, the apparatus comprising: a base having a top portion and a bottom portion, the base configured to be affixed to a patient via the bottom portion; at least one grommet secured within an aperture in the base; and at least one filler grommet configured to be secured within the aperture in the base, wherein the at least one filler grommet and at least one grommet are configured to attach the medical device to the base to hold the medical device in place during the medical procedure.

In certain embodiments, the apparatus further comprises a gasket, the gasket configured to be secured within the aperture in the base.

In certain embodiments, the bottom portion of the base is secured to the patient via adhesive, micro-suction, glue and combinations thereof.

In certain embodiments, the bottom portion of the base is secured to the patient via an adhesive pad, the adhesive pad occupying approximately ⅔ of a surface area of the bottom portion of the base.

In certain embodiments, approximately ⅓ of the bottom portion of the base includes micro-suction adhesive material and a seating hole of the medical device.

In certain embodiments, the medical device is selected from a group consisting of a needle decompression catheter for chest decompression, a central venous catheter, Turkel catheter, Tenckhoff catheter, Hemodialysis catheter, Hickman line, Groshong line, Quinton catheter, Huber needle, percutaneous endoscopic gastronomy feeding tube, peripherally inserted central catheter, intrauterine pressure catheter, pulmonary artery catheter, Swan-Ganz catheter, and suprapubic catheter.

In certain embodiments, the apparatus is pre-attached to the intended medical device being inserted into the patient. This allows for an even more streamlined application of the invention and requires integration with an existing medical device from the group listed above.

In certain embodiments, the at least one filler grommet has an outer diameter slightly smaller than a slightly larger inner diameter of the grommet.

In certain embodiments, there is a physical connection between the grommet and the filler grommet.

In certain embodiments, the apparatus further comprises at least one clip ring and at least one adhesive strip attached to the base adjacent to the grommet and extending away from the grommet, the at least one clip able to support varying lengths of the medical apparatus.

In certain embodiments, the at least one clip ring is slidable on the adhesive strip.

In certain embodiments, the base is a rigid body or a flexible base.

In certain embodiments, the at least one grommet and the at least one filler grommet are shaped as ellipses, squares, triangles, hexagons, circles, and combinations thereof.

In certain embodiments, the filler grommet is attached to the base via a wire or cord.

In certain embodiments, the grommet, rings, or gaskets are made from rubber, plastic, silicone, and combinations thereof.

In certain embodiments, the apparatus is three dimensionally printed and thereby customized to conform to the patient.

In certain embodiments, the apparatus is made via additive manufacturing techniques.

Other objects of the invention are achieved by providing a method for securing a medical device to a patient during a medical procedure, the method comprising the following steps: providing an apparatus; securing the base to a skin surface of a patient; inserting the medical device into the patient through the aperture in the base; inserting the grommet into the base; and inserting the filler grommet within the aperture in the base, wherein the at least one filler grommet and at least one grommet attach the medical device to the base.

In certain embodiments, the method includes inserting a gasket into the aperture in the base to secure the at least one grommet to the filler grommet.

In certain embodiments, the bottom portion of the base is secured to the patient via adhesive, micro-suction, glue and combinations thereof.

In certain embodiments, the method includes providing at least one clip ring and at least one adhesive strip attached to the base adjacent to the grommet and extending away from the grommet, the at least one clip able to support varying lengths of the medical apparatus.

In certain embodiments, the method includes sliding the at least one clip ring on the adhesive strip to support the varying lengths of the medical apparatus.

Other objects of the invention are achieved by providing silicon rubber on plastic friction mechanisms to secure the catheter.

In certain embodiments, an aperture base is designed to allow catheters of many sizes, small to large, while the dimension range is not too large so as to allow excessive movement.

It in certain embodiments, it is contemplated that additional features for securing the tubing can be supplemented onto the device to accommodate outlier medical devices or medical devices having unique configurations.

Other objects of the invention are achieved by providing an apparatus for securing a medical device to a patient designed with superior adhesion technology to sustain high traffic and disturbance areas. The oil effusing, soft and malleable skin surface of a patient presents a difficult area to secure, especially during strong perturbations, such as those experienced during chest decompressions. Recent advances in micro-suction and other medical adhesive technologies such as double coating allow the base to reliably attach to any patient on almost any point of their anatomy Other objects of the invention are achieved by providing an apparatus that would require only a single person as opposed to the multiple personnel needed for current attempts to secure needle decompression catheters.

Other objects of the invention are achieved by providing an apparatus that would allow for specific depth placement and retention at said depth of medical devices. This would obviate the need for the "burying/tunneling" of the Turkel catheter, which reduces the risk of harming internal tissues or organs. This versatile innovation also precludes the need for excessive sutures and surgical methods for securing the catheter that would add unnecessary risk to the patient.

Objects of the invention are achieved by providing systems, devices and methods which include a coating selected from the group consisting of an anti-microbial, an anti-bacterial, an anti-hemorrhagic agent, and combinations thereof.

Objects of the invention and its particular features and advantages will become more apparent from consideration of the following drawings and accompanying detailed description. Variations from the description above may and can be made by one skilled in the art without departing from the scope of the invention. It should be understood that the detailed description and specific examples, while indicating the preferred embodiment of the invention, are intended for purposes of illustration only and are not intended to limit the scope of the invention.

DETAILED DESCRIPTION OF THE INVENTION

In the following description, numerous details are set forth for the purpose of example and explanation; however, one of ordinary skill in the art will realize that the invention may be practiced without the use of these specific details. The device as shown involves a catheter securing that utilizes a plastic-on-rubber friction dependent bond. However, other medical devices may be used with the apparatus and system of the present invention.

The Appendix to the application is incorporated by reference herein in its entirety.

Figure 1:
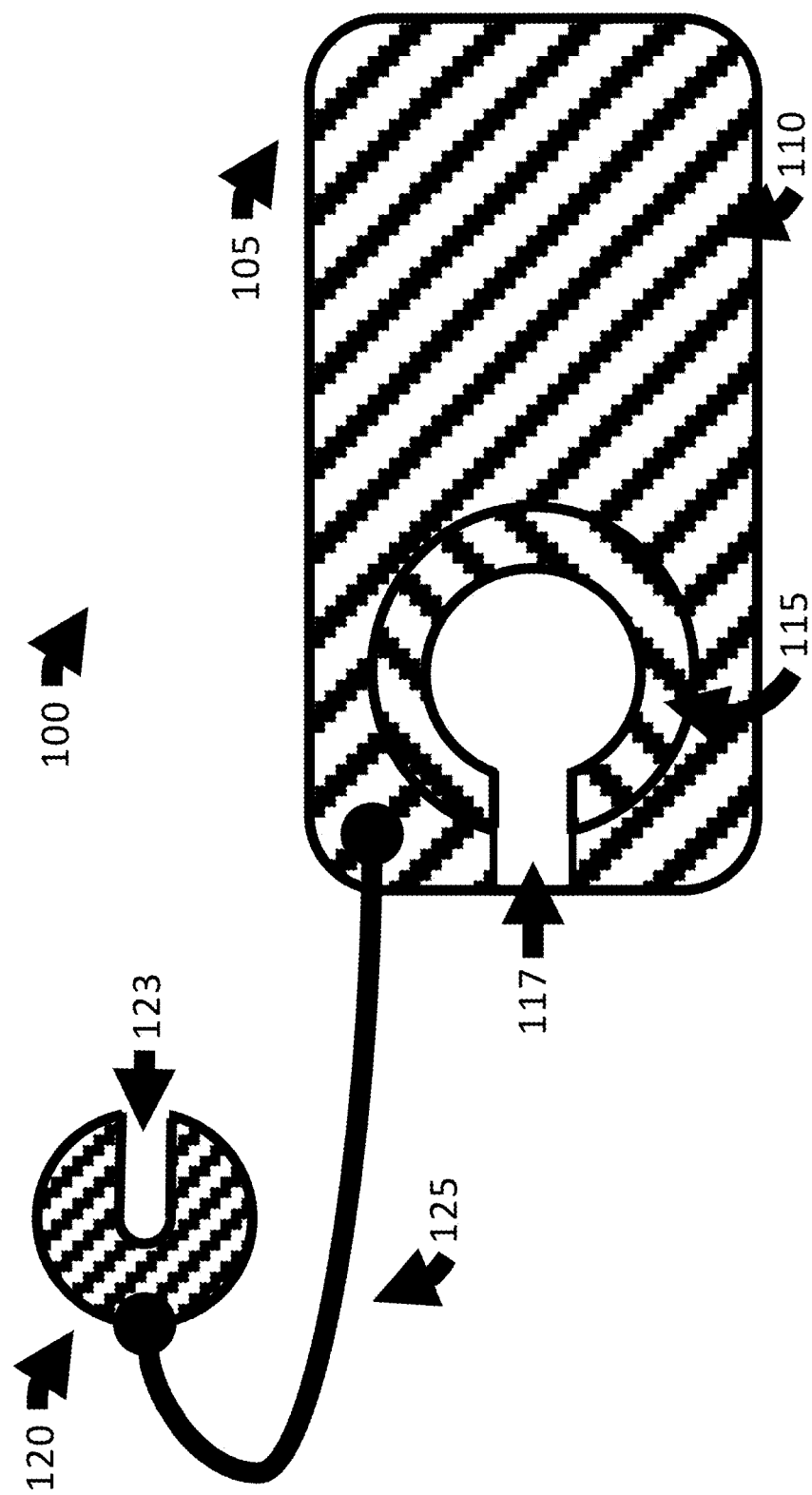
FIG. 1 is a top schematic diagram depicting an embodiment of the inventive method and system.
Figure 2:
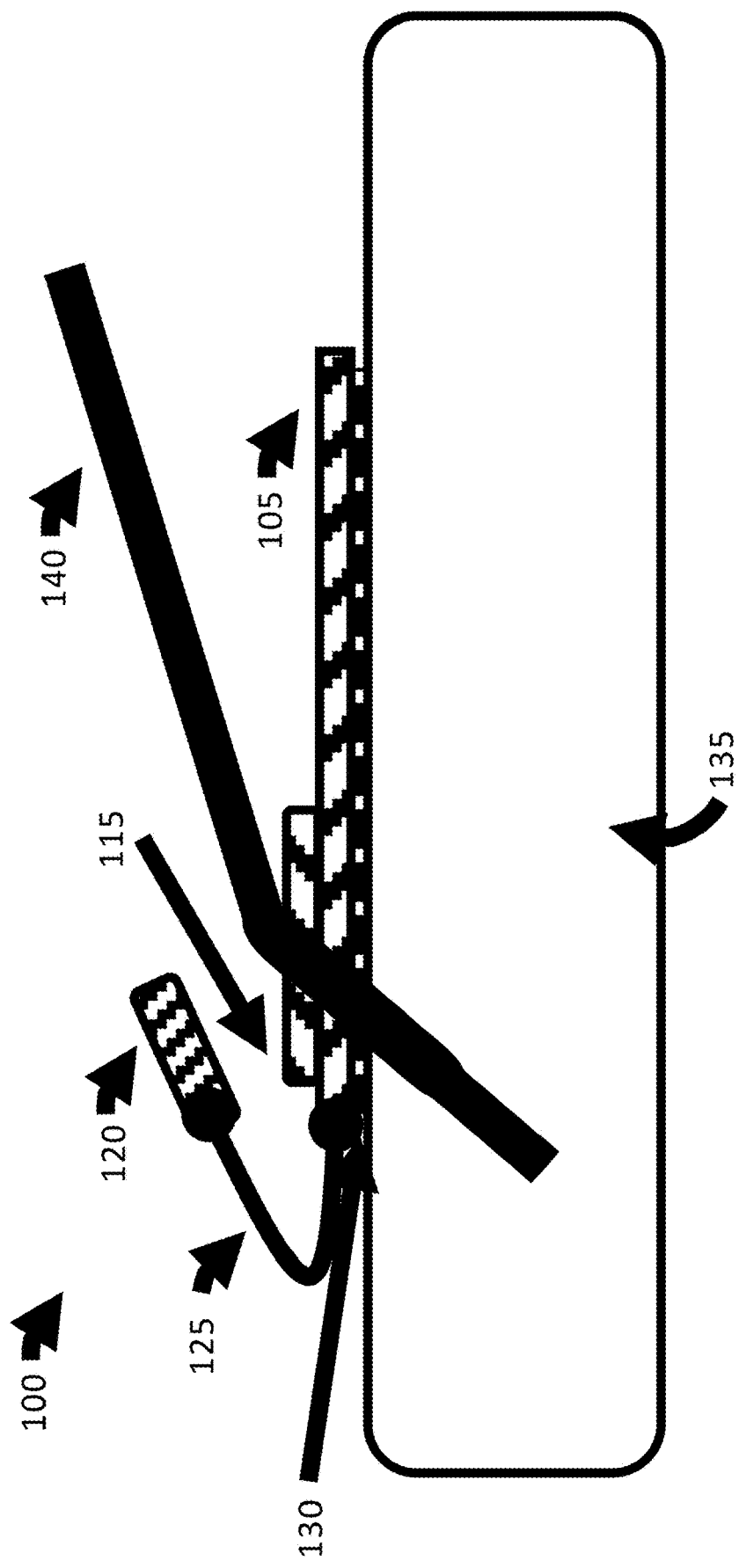
FIG. 2 is a side-view schematic diagram depicting an embodiment of the inventive method and system.
Figure 3A:
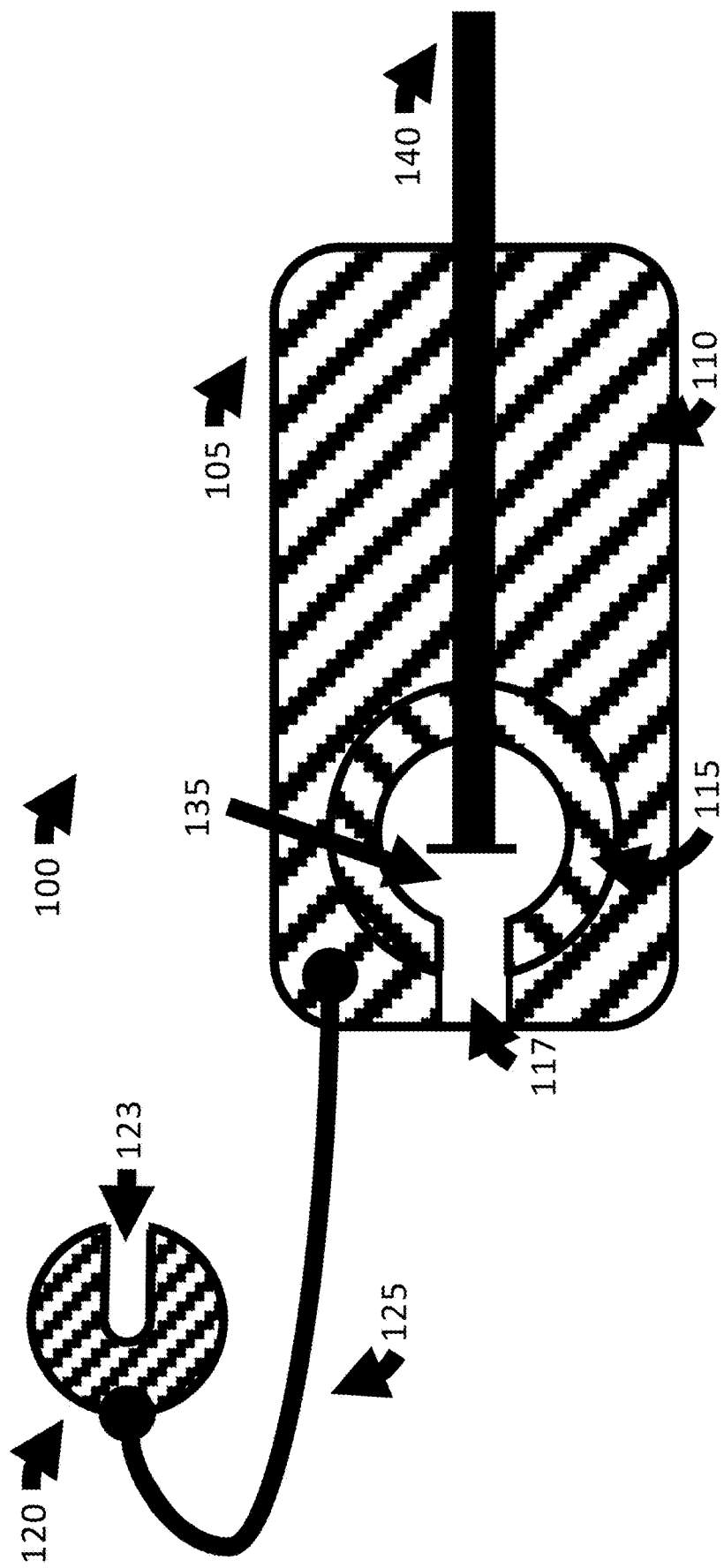
FIGS. 3A & 3B are schematic diagrams depicting embodiments of the inventive method and system while securing a catheter.
Figure 3B:
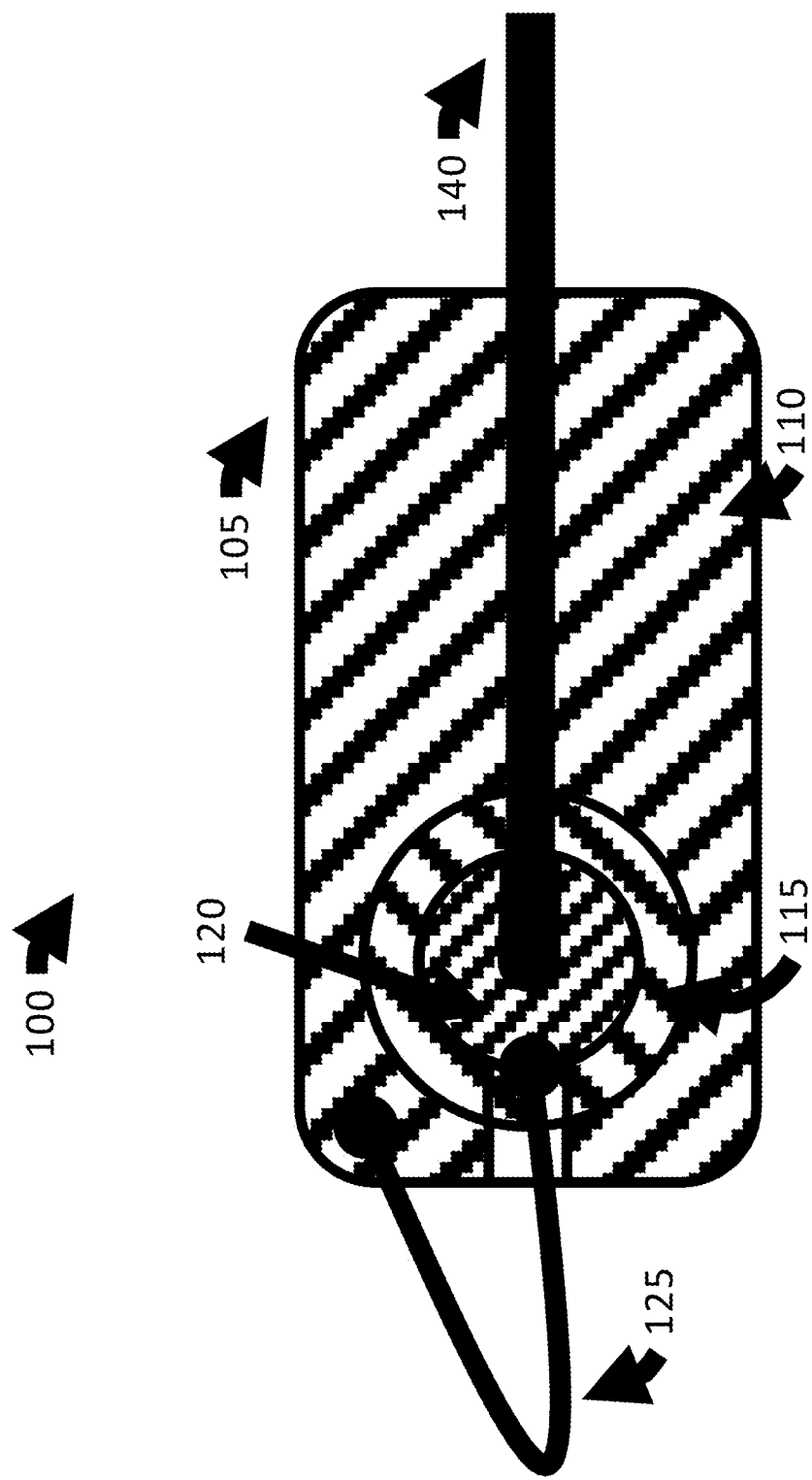
Figure 4:
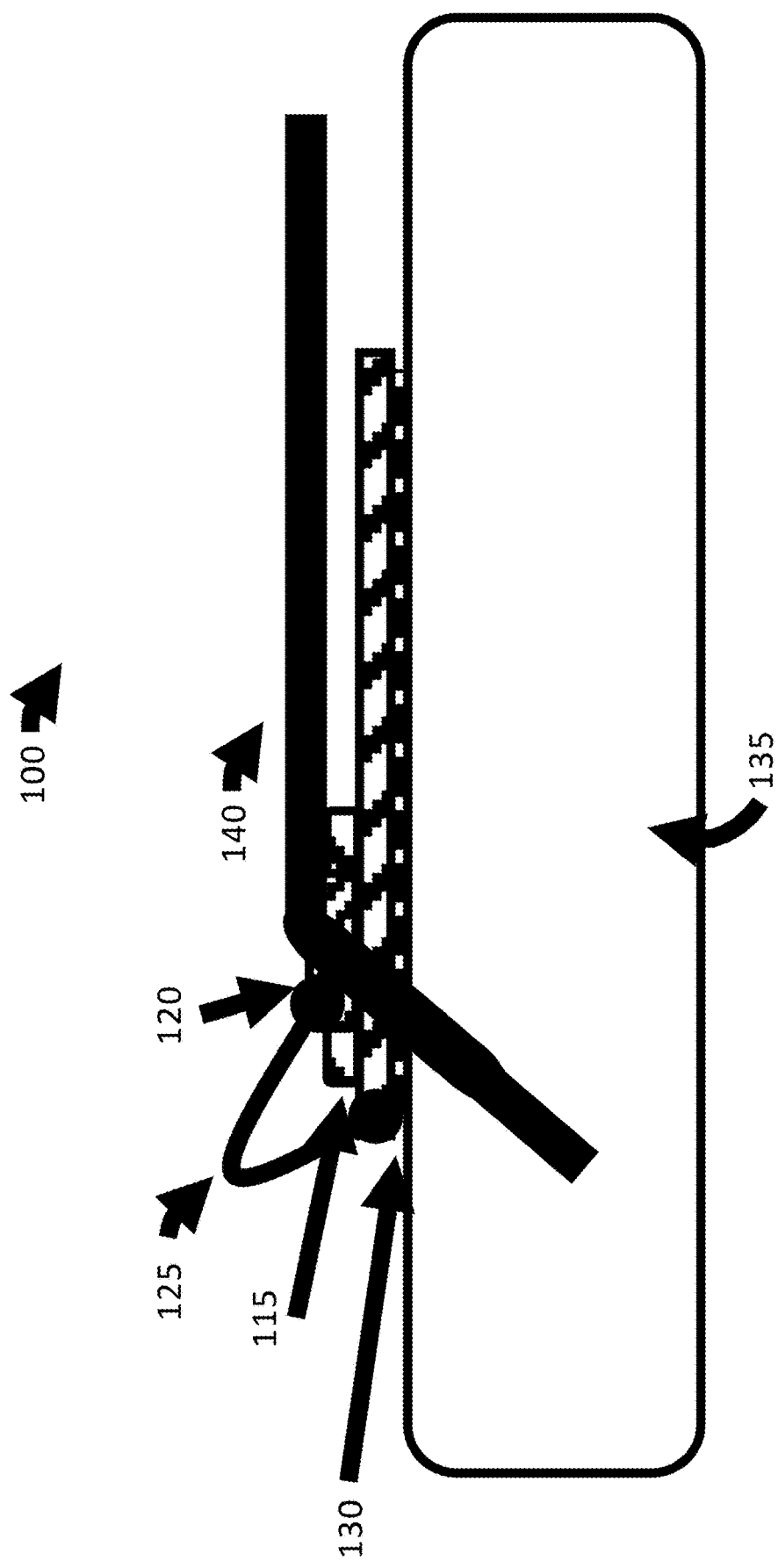
FIG. 4 is a side-view schematic diagram depicting embodiments of the inventive method and system while securing a catheter.

As depicted in FIG. 1 and FIG. 2, an embodiment of the inventive method and system (100) includes a flexible or semi flexible base or pad (105) having a top portion (110) a first grommet (115) affixed to the base (105) and a second "filler" grommet (120) optionally connected to the base (105) with and by a tether (125). It is contemplated that the first and second grommets (115, 120) include cut-out portions (117 and 123 respectively) to provide access of the optional tether (125) and/or a catheter or lumen (140).

It is contemplated that the base (105) includes a medical adhesive (130) to removably affix the base (105) to a patient (135). Depending upon the medical circumstances, the base (105) may be affixed to a patient (135) before or after a catheter or lumen (140) is placed in a patient (135). In certain embodiments, portions of the base (105) may include a medical adhesive (130), such as ⅓ of the base or ⅔ of the base. In various embodiments, different mechanisms are used to secure the base to the patient.

As depicted in FIGS. 3A, 3B, 4, and 5, after a catheter or lumen (140) is placed within a patient (135) and the base (105) affixed to the patient (135), the second grommet is removably secured within the first grommet (115) via a press or friction fit and/or medical adhesive (not shown). It is contemplated that the dimensional configuration of the second grommet (120) provides frictional tension between the catheter or lumen (140) and the first grommet (115), thus mitigating or preventing the catheter or lumen (140) from being inadvertently removed or dislodged from a patient (135) while preventing an excessive degree of arc or bend to the catheter or lumen (140). It is contemplated that medical adhesive (not shown) may also be used to removably secure or affix the second grommet (120) to the first grommet (115) and/or the catheter or lumen (140).

Figure 5:
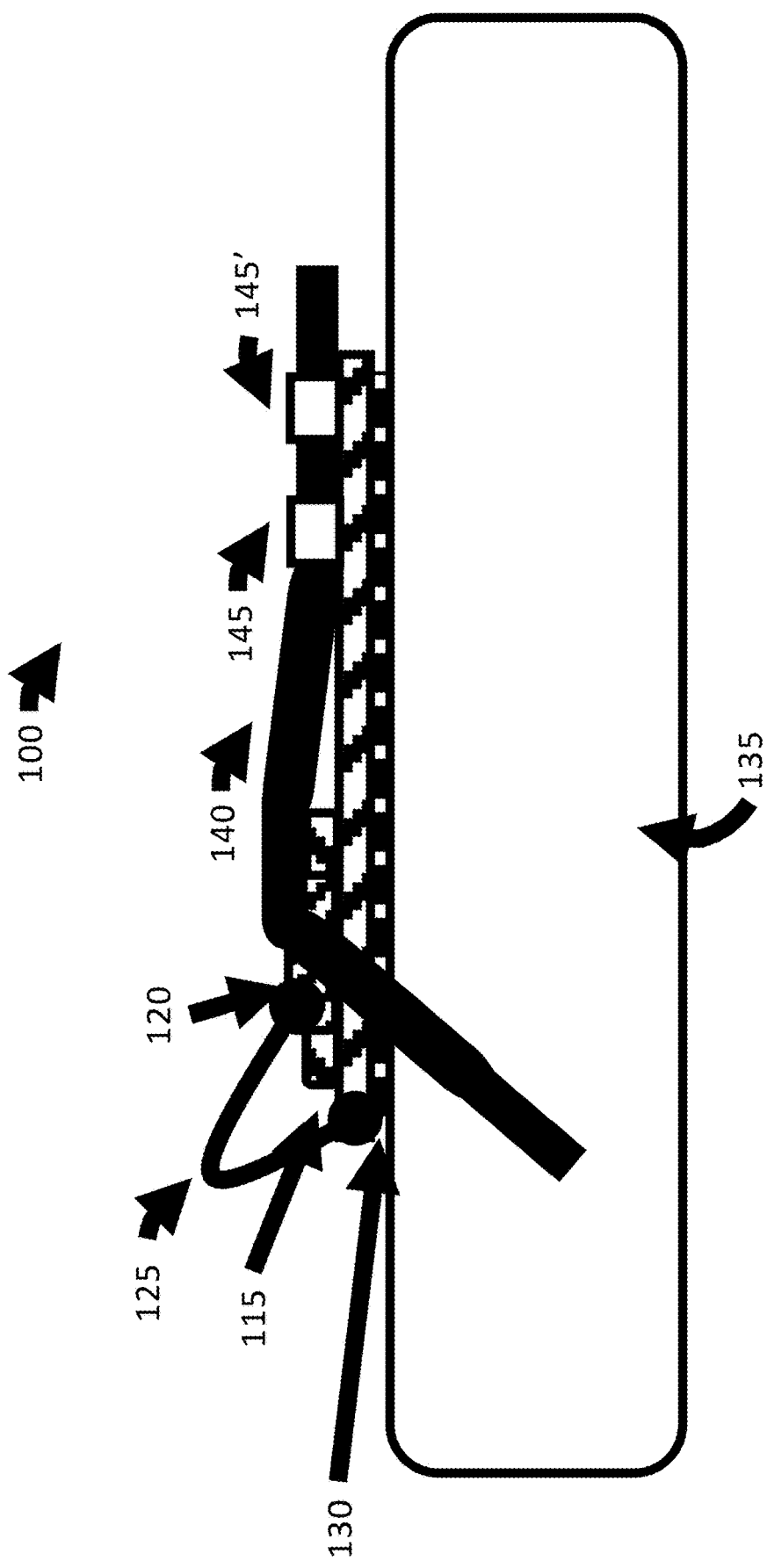
FIG. 5 is a side-view schematic diagram depicting embodiments of the inventive method and system while securing a catheter with additional straps.
Figure 6:
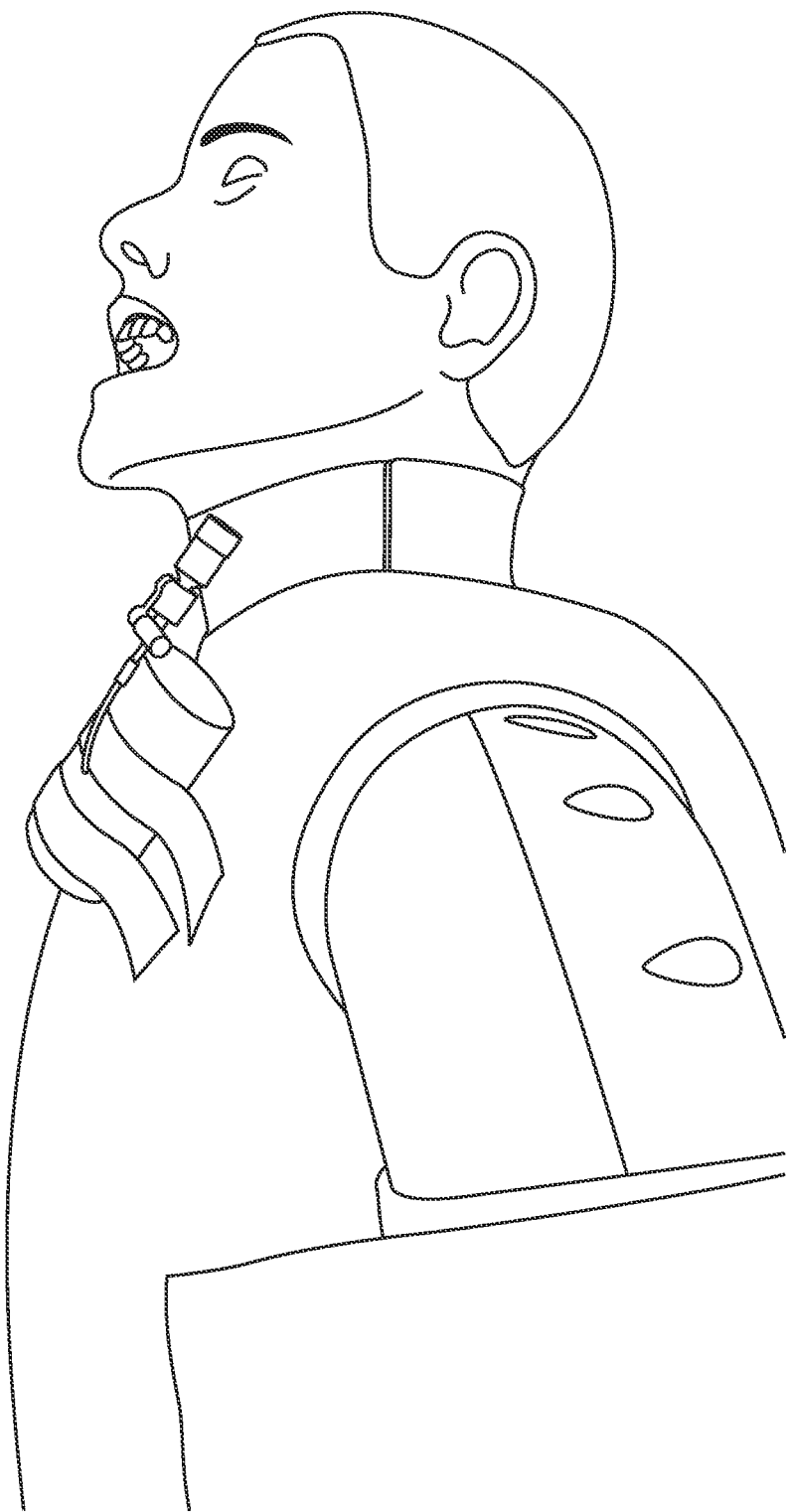
FIGS. 6-11 are photographs of an embodiment of the inventive method and system.
Figure 7:
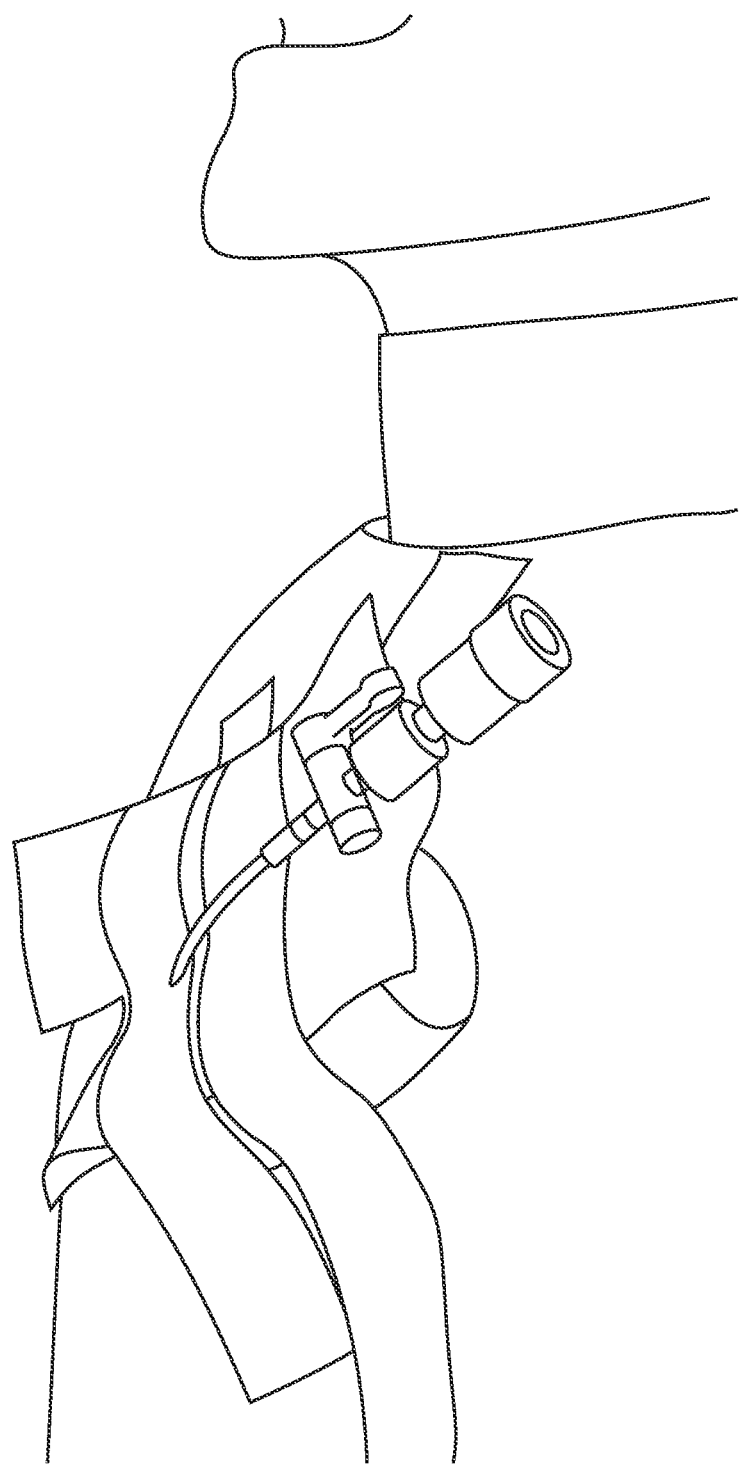

As depicted in FIG. 5, the base (105) may include clips, grommets, or hollow gaskets (145, 145') to further secure the catheter or lumen (140) to the base (105) also providing "strain relief" to the first and second grommets (115, 120).

It is contemplated that the system is intended to secure the catheter (140) after a chest decompression has been performed. To this end, the base (105) of the system has been designed to securely attach to the patients' chest and sustain substantial external forces that are diffused over the wide surface area and multiple points of contact. The adhesive material (130) assists in this regard and can be selected to optimize either the stability or flexibility of placement.

It is contemplated that the device saves time vs the old method of securement. To this end, simple components that are easy to manipulate by a single personnel were included. The plastic and silicon grommets are rapidly connected, thereby securing the catheter and completing the method in a fraction of the time typically used to tape and gauze the exposed tubing. Additionally, the device can be pre-attached to the medical device intended for securement before it is even inserted, thereby saving even more time during the procedure.

It is contemplated that the device secures the catheter in a manner that still allows full utilization but allows it to no longer interfere with other treatments. Apertures in the rubber grommets are able to guide the external portion of the tubing, allowing full functional use, and preventing bends or kinks that would otherwise risk occluding the flow of materials through the tube. Additionally, the base can be flexible or rigid depending on which accommodates the anatomy of the catheter site better. It is contemplated that certain embodiments of the invention will include a three dimensionally printed base that is tailored to the patient's anatomy, thereby achieving a more perfect fit and maintaining full utilization of the catheter.

It is contemplated that the invention uses silicon rubber on plastic friction mechanism to secure a catheter to a patient.

In certain embodiments, the device includes superior adhesion for high traffic/disturbance area.

In certain embodiments, the gasket is specially designed to stop kinking of Turkel as it bends and helps prevent hubs of (top of) 14 gauge needle decompression catheters from folding over and being useless/ineffective for treatment.

In certain embodiments, the device has various shapes and configurations but operates via a principle of operation of attaching a medical device, such as a catheter, to a patient without the need for tape or gauze.

In certain embodiments, the device has a grommet and filler grommet having a circular or disc like shape and having an aperture at one end of the circular or disc like shape. In such an embodiment, a catheter can be slide into the aperture in the grommet and filler grommet, and the catheter can be held in place by frictional forces.

In certain embodiments, the catheter is force fit within the aperture in the grommet and filler grommet.

In certain embodiments, the device is made or rubber, silicon or other materials.

In certain embodiments, the adhesive to secure the device to a patient is a hydrogel adhesive.

In certain embodiments, the bottom portion of the device has a liner that can be pulled to expose the adhesive and stick the device onto a patient.

In certain embodiments, a strap is attached at one end to the base along with an accompanying loop that is attached longitudinally on the base, wherein the strap is tapered so that the unattached end is slightly wider than the loop opening. This allows the user to easily secure the exposed end of the medical tubing securely to the base by pulling the strap through the accompanying loop, thus securing the strap in place.

In certain embodiments, a holding member is secured via an adhesive to the base wherein a strap is secured at one end to a holding member. In certain embodiments, the strap is secured at one end under the holding member.

Components of Embodiment of System

Figure 8:
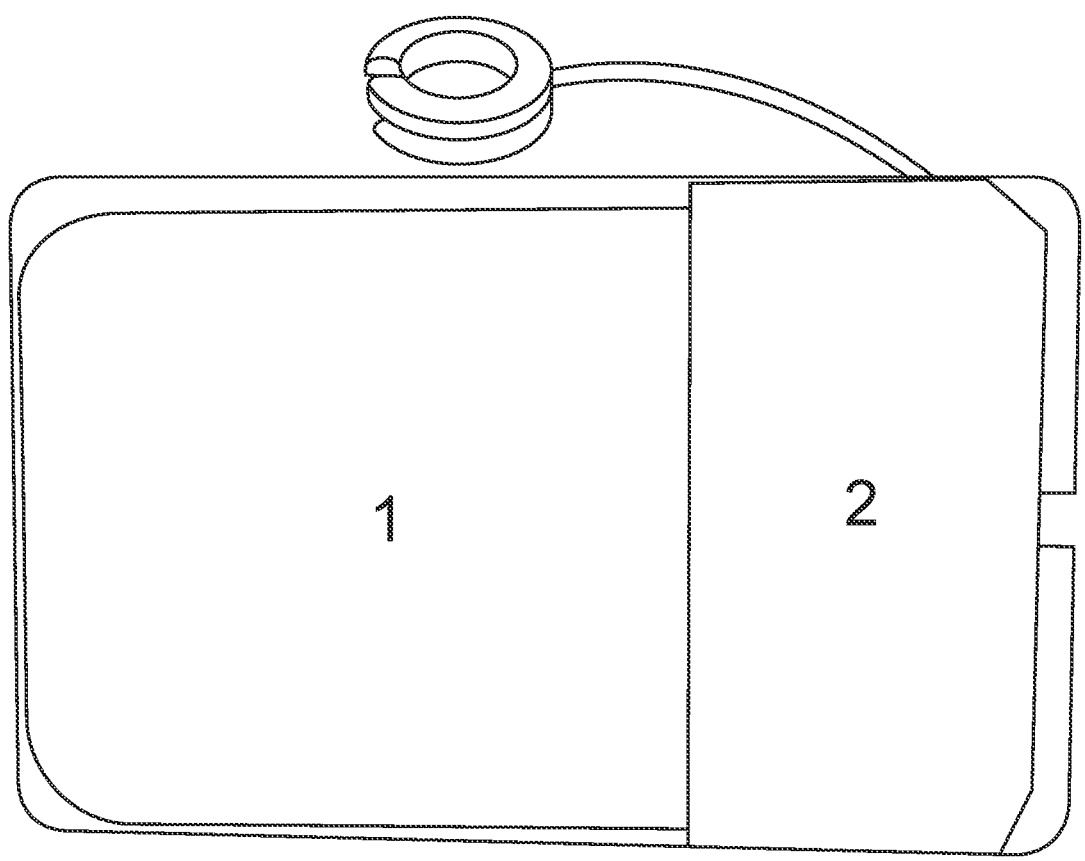
Figure 9:
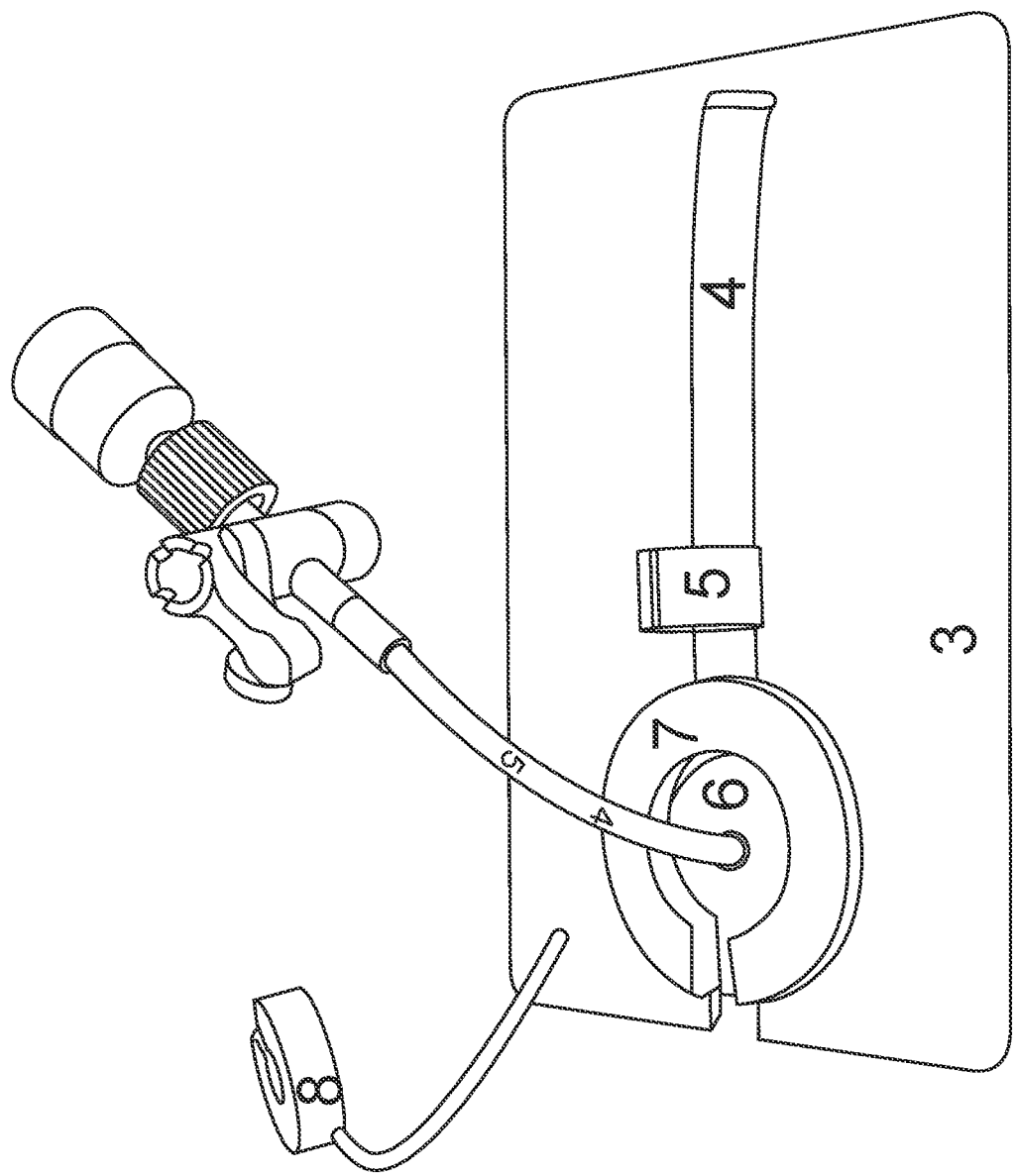
Figure 10:
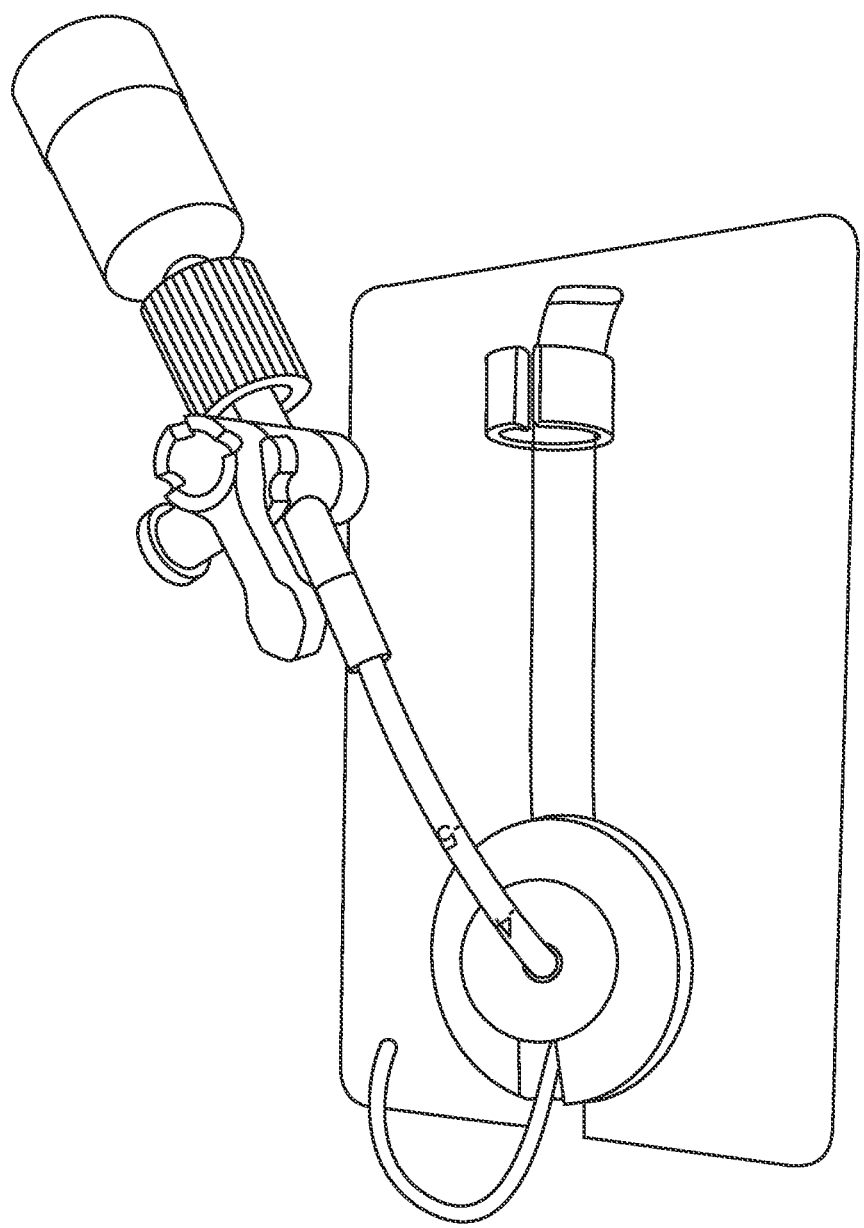
Figure 11:
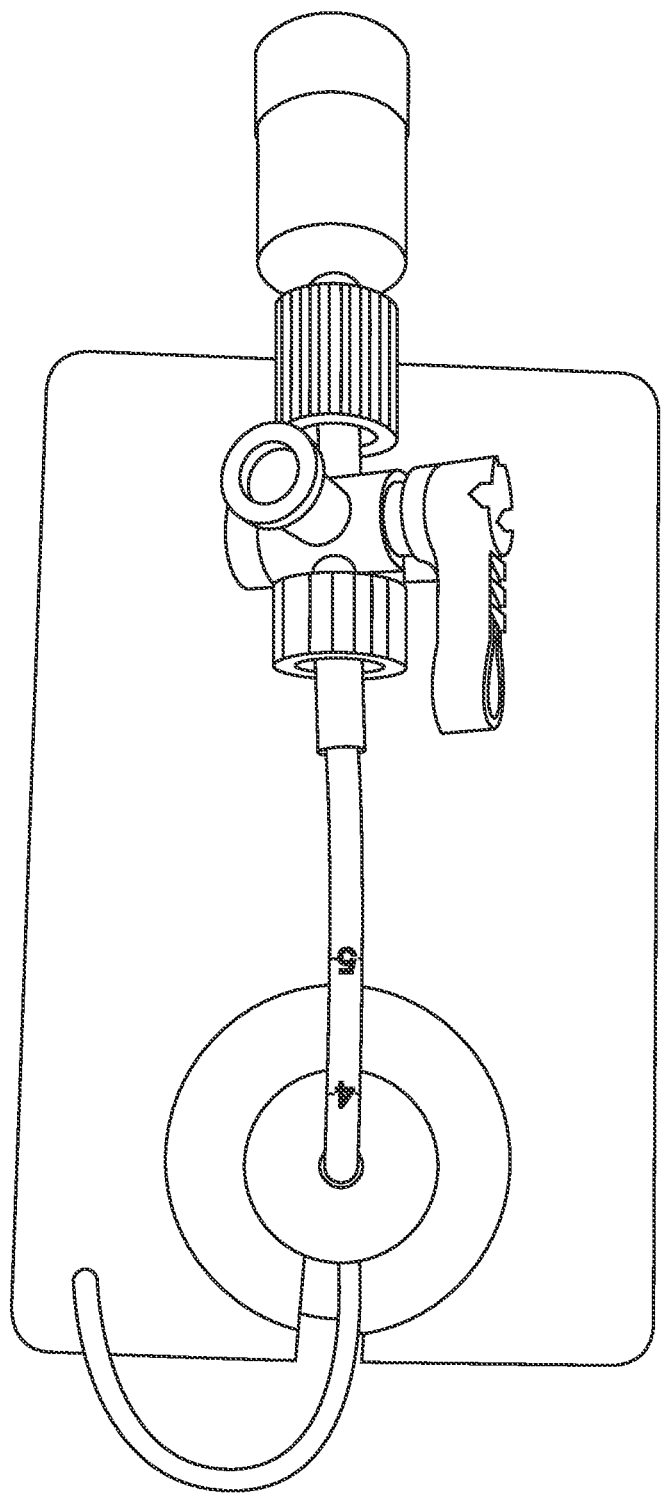

In certain embodiments, system has various parts as shown in FIGS. 6-11. In FIGS. 8-9, the parts are numbered namely:

Part 1—adhesive pad with tensile strength similar to that of a defibrillation pad. Occupies approximately ⅔ of underside of device. Part 1 is used for anchoring device to patient.

Part 2—Micro-suction adhesive material with a cut to allow for easy placement and a seating hole for catheter. Part 2 still retains adhesiveness after several uses is wiped off with alcohol prep or water. Part 2 adheres to catheter and filler grommet.

Part 3—Standard size (CR80) plastic PVC card/pad with 20-30 mil thickness with a funnel slot cut into one end to feed catheter to center of ⅝ hole also cut into the plastic. This card has two more small cuts. One unseen under part 7 and one slightly from the top. Part 4 is fed through these last two mentioned slots.

Part 4—Plastic strip cut from 0.007 thickness clear plastic. Woven through two slits cut into plastic card/pad. Part 4 is the anchoring system for part 5.

Part 5—Plastic 8 mm diameter clip rings. These rings can be locked and unlocked with ease. This clip slides along length of plastic strip based on clinicians need as the amount of catheter exposed will vary from patient to patient.

Part 6—A ⅝ diameter hole cut to allow catheter to be fed into micro suction adhesive pad which lies beneath this hole. Also used for part 7 to surround the catheter.

Part 7—A rubber/plastic/silicone o ring or gasket type ring. Surrounds part 6 and holds part 8. Also serves as a cushion and protector for the catheter when it is laid down to be secured.

Part 8—Filler and holder grommet. Has a small triangle section removed to feed catheter through with a seating hole slightly smaller than then diameter of the catheter to create plastic on plastic "friction bond". After being placed around catheter it is snuggly fit into the O-ring gasket. The micro-suction adhesive adheres to aid in the retention created by the snug fit. This grommet attaches to card/pad via a length of silicone akin to a small headphone wire. This length of silicone is attached through a small hole in the base of the device.

Method of Operation

In certain embodiments, the method involves first removing the adhesive protector from micro-suction pad.

The second step involves feeding the base of exposed portion of catheter into seating hole in micro-suction pad via slot.

The third step involves removing the adhesive back of anchoring pad.

The fourth step involves applying the anchoring pad to patient.

The fifth step involves attaching the holder grommet to catheter with small triangle cut facing towards the 8 mm plastic clip and slide mechanism.

The sixth step involves firmly seating the catheter into O-ring.

The seventh step involves sliding 8 mm clip to appropriate point for remaining length of catheter.

The eighth step involves opening the and securing it shut around the catheter.

Additional Inventive Features and Components of System

In certain embodiments, instead of the filler grommet attached to the base of the card, a strip of adhesive material is used to wrap around the base of the catheter.

In certain embodiments, the device can be adjusted to fit varying lengths of a catheter and can be used to secure the catheter to a patient.

The anchoring system replaces an archaic and ineffective means for securing a unique type of catheter. Due to the uniqueness of the catheter, i.e. size, variable depth of placement, and heaviness, it requires a means of securing that is only made possible by the device described herein. The device addresses and resolves a long-standing problem by way of the above noted reasons.

The device also establishes a new principle of operation. It not only eliminates the bulk, but it also provides an adaptive means of securing the top-heavy portion of the catheter, whether there is unused length or the entirety of the catheter is inserted.

The device is configured to accommodate and secure the variance in utilized length specific to heavy catheters. This variance can be substantial depending on the function of the catheter and where it is placed on the patient.

In certain embodiments, alternate clear plastic strap having adhesive ends is provided that secures the remaining length of the catheter. In certain embodiments, this is an alternative to the 8 mm diameter clip rings.

In one or more embodiments the method further comprises sliding the at least one clip ring on the adhesive strip to support the varying lengths of the medical apparatus.

TABLE 1

Different Types of Catheters and Their Medical Purpose.

| Type of Catheter | Purpose |
| --- | --- |
| Central venous catheter (CVC) | Central line access |
| Turkel catheter | Centesis (fluid drain) |
| Tenckhoff | Ascites drain with on/off switch |
| Hemodialysis catheter | Dialysis; requires two lumen |
| Hickman line | Chemotherapy (also dialysis and central) |
| Groshong line | Three-way valve for central line |
| Quinton catheter | Temporary hemodialysis (untunneled) |
| Huber needle | Chemotherapy |
| Percutaneous endoscopic gastronomy (PEG) | Feeding tube |
| Peripheral insertion central catheter (PICC) | Peripheral insertion |
| Intrauterine pressure catheter (IUPC) | Uterus pressure during contractions |
| Pulmonary artery catheter (PAC) | Swan-Ganz; large vein |
| Suprapubic cystotomy | Bladder drainage (laproscopic) |
| Ports (surgically installed with tunneling) | Insulin and chemotherapy infusion |
| Fogarty embolectomy | Balloon inflates to remove clot |
| Foley catheter | Bladder drainage (urethra) |

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

The invention claimed is:

1. An apparatus for securing a medical device to a patient during a medical procedure, the apparatus comprising:
   a base having a top portion and a bottom portion, the base configured to be affixed to a patient via the bottom portion;
   at least one grommet secured within an aperture in the base; and
   at least one filler grommet configured to be secured within the aperture in the base,
   wherein the at least one filler grommet and at least one grommet are configured to attach the medical device to the base to hold the medical device in place during the medical procedure,
   wherein the at least one filler grommet has an aperture that allows the at least one medical device to pass through the aperture of the at least one filler grommet, and wherein the at least one filler grommet is removably secured within the at least one grommet via a press or friction fit.

2. The apparatus of claim 1, wherein the bottom portion of the base is configured to be secured to the patient via adhesive, micro-suction, glue and combinations thereof.

3. The apparatus of claim 1, wherein the medical device is selected from a group consisting of a needle decompression catheter for chest decompression, a central venous catheter, Turkel catheter, Tenckhoff catheter, Hemodialysis catheter, Hickman line, Groshong line, Quinton catheter, Huber needle, percutaneous endoscopic gastronomy feeding tube, peripherally inserted central catheter, intrauterine pressure catheter, pulmonary artery catheter, Swan-Ganz catheter, and suprapubic catheter.

4. The apparatus of claim 1, wherein the at least one filler grommet has an outer diameter slightly smaller than a slightly larger inner diameter of the at least one grommet.

5. The apparatus of claim 1, wherein there is a physical connection between the at least one grommet and the at least one filler grommet.

6. The apparatus of claim 1, wherein the at least one filler grommet is attached to the base via a wire or cord.

7. The apparatus of claim 1, wherein a strap is attached at one end to the base along with an accompanying loop that is attached longitudinally on the base, wherein the strap is tapered so that the unattached end is slightly wider than the loop opening.

8. The apparatus of claim 1, wherein the medical device intended for insertion into the patient is pre-attached to the apparatus.

9. The apparatus of claim 1, further comprising at least one clip ring and at least one adhesive strip attached to the base adjacent to the at least one grommet and extending away from the at least one grommet, the at least one clip ring able to support varying lengths of the medical device.

10. The apparatus of claim 9, wherein the at least one clip ring is slidable on the adhesive strip.

11. The apparatus of claim 1, wherein the base is a rigid body or a flexible base.

12. The apparatus of claim 1, wherein the at least one grommet and the at least one filler grommet are shaped as ellipses, squares, triangles, hexagons, circles, and combinations thereof.

13. The apparatus of claim 1, wherein the at least one grommet or the at least one filler grommet are made from rubber, plastic, silicone, and combinations thereof.

14. The apparatus of claim 1, wherein the apparatus is three dimensionally printed and thereby customized to conform to the patient.

15. A method for securing a medical device to a patient during a medical procedure, the method comprising the following steps:
providing an apparatus according to claim 1;
securing the base to a skin surface of a patient;
inserting the medical device into the patient through the aperture in the base;
inserting the at least one grommet into the base; and
inserting the at least one filler grommet within the aperture in the base,
wherein the at least one filler grommet and at least one grommet attach the medical device to the base.

16. The method of claim 15, wherein the bottom portion of the base is secured to the patient via adhesive, micro-suction, glue and combinations thereof.

17. An apparatus for securing a medical device to a patient during a medical procedure, the apparatus comprising:
a base having a top portion and a bottom portion, the base configured to be affixed to a patient via the bottom portion;
at least one grommet secured within an aperture in the base; and
at least one filler grommet configured to be secured within the aperture in the base,
wherein the at least one filler grommet and at least one grommet are configured to attach the medical device to the base to hold the medical device in place during the medical procedure,
wherein the bottom portion of the base is configured to be secured to the patient via an adhesive pad, the adhesive pad occupying approximately ⅔ of a surface area of the bottom portion of the base, and
wherein approximately ⅓ of the bottom portion of the base includes the aperture of the base and a micro-suction adhesive material.

* * * * *